United States Patent
Roemisch et al.

(10) Patent No.: US 12,274,738 B2
(45) Date of Patent: Apr. 15, 2025

(54) FX ACTIVATION PROCESS AND ITS USE IN THE PREPARATION OF A FXA COMPOSITION

(71) Applicant: OCTAPHARMA AG, Lachen (CH)

(72) Inventors: Juergen Roland Roemisch, Gramatneusiedl (AT); Katharina Pock, Vienna (AT); Petra Schulz, Vienna (AT); Silvio Wuschko, Vienna (AT); Michael Andesner, Vienna (AT); Andrej Muranyi, Vienna (AT)

(73) Assignee: OCTAPHARMA AG, Lachen (CH)

( * ) Notice: Subject to any disclaimer, the term of this patent is extended or adjusted under 35 U.S.C. 154(b) by 845 days.

(21) Appl. No.: 17/257,705

(22) PCT Filed: Jul. 8, 2019

(86) PCT No.: PCT/EP2019/068293
§ 371 (c)(1),
(2) Date: Jan. 4, 2021

(87) PCT Pub. No.: WO2020/008079
PCT Pub. Date: Jan. 9, 2020

(65) Prior Publication Data
US 2021/0290738 A1  Sep. 23, 2021

(30) Foreign Application Priority Data

Jul. 6, 2018 (EP) .................... 18182242
Jan. 24, 2019 (EP) .................... 19153624

(51) Int. Cl.
*A61K 38/36* (2006.01)
*A61K 38/48* (2006.01)
*C07K 1/36* (2006.01)
*C07K 1/18* (2006.01)
*C07K 1/22* (2006.01)

(52) U.S. Cl.
CPC ...... *A61K 38/4846* (2013.01); *A61K 38/4833* (2013.01); *C07K 1/36* (2013.01); *C07K 1/18* (2013.01); *C07K 1/22* (2013.01); *C12Y 304/21005* (2013.01); *C12Y 304/21006* (2013.01)

(58) Field of Classification Search
None
See application file for complete search history.

(56) References Cited

U.S. PATENT DOCUMENTS

2003/0232075 A1  12/2003 Nelsestuen
2016/0046922 A1* 2/2016 Hasslacher .......... C12N 9/6432
                                              435/226

FOREIGN PATENT DOCUMENTS

CN  106413744  2/2017
CN  107460182  12/2017
EP  0 129 998  1/1985

OTHER PUBLICATIONS

Lollar et al., "Stabilization of thrombin-activated porcine factor VIII:C by factor IXa phospholipid" Blood, Jun. 1984;63(6):1303-8. PMID: 6426549.*
Majumder et al., Biophys J. Feb. 2003;84(2 Pt 1):1238-51. doi: 10.1016/S0006-3495(03)74939-X PMID: 12547804 PMCID: PMC1302700.*
Le Bonniec et al., J Biol Chem. Apr. 5, 1992;267(10):6970-6. PMID: 1551906.*
"Human Factor Xa REF 526", Sekisui Diagnostics, LLC, Jan. 1, 2012, p. 1, XP055963795, Retrieved from the Internet: URL:https://www.invitech.co.uk/index.php?route=product/attachmanager/getfile&product_attach_file_id=3703.
"Coagulation Factor Xa, Human Plasma CAS 9002-05-5 233526", Mar. 19, 2009, XP055963635, Retrieved from the Internet: https://www.merckmillipore.com/DE/de/product/Coagulation-FactorXa-Human-Plasma,EMD_BIO-233526?ReferrerURL=https://www.google.com/#anchor_PDS.
Lollar et al., "Activation of Porcine Factor VIII:C by Thrombin and Factor Xa", Biochemistry, 24(27): 8056-8064 (1985).
International Search Report and Written Opinion of the International Searching Authority, issued Nov. 6, 2019 in corresponding International Patent Application No. PCT/EP2019/068293.
Koklic et al., "$Ca^{2+}$ Switches the Effect of PS-containing Membranes on Factor Xa from Activating to Inhibiting: Implications for Initiation of Blood Coagulation", Biochem. J. 462(3): 591-601 (2014).
Majumder et al., "Soluble Phosphatidylserine Binds to Two Sites on Human Factor IXa in a $Ca^{2+}$ Dependent Fashion to Specifically Regulate Structure and Activity", PLoS One, 9(6): e100006, pp. 1-10, XP055592949 (2014).
Bom et al., "The contributions of $Ca^{2+}$, phospholipids and tissue-factor apoprotein to the activation of human blood-coagulation Factor X by activated Factor VII", Biochem. J., 265(2): 327-336 (1990).

* cited by examiner

*Primary Examiner* — Michael Szperka
(74) *Attorney, Agent, or Firm* — Wenderoth, Lind & Ponack, L.L.P.

(57) ABSTRACT

The invention relates to a high purity Coagulation Factor Xa (FXa or activated Coagulation Factor X) preparation and an activation and purification process to obtain said FXa of high purity and high degree of activation without addition of proteinaceous activators during manufacturing.

20 Claims, 5 Drawing Sheets

FX ACTIVATION PROCESS AND ITS USE IN THE PREPARATION OF A FXA COMPOSITION

TECHNICAL FIELD OF THE INVENTION

The invention relates to a high purity coagulation Factor Xa (FXa or activated coagulation Factor X) preparation and an activation and purification process to obtain said FXa of high purity and high degree of activation without addition of proteinaceous activators during manufacturing.

BACKGROUND OF THE INVENTION

Coagulation Factor Xa (FXa) is a two-chain glycoprotein generated by activation of its vitamin K dependent zymogen coagulation Factor X (FX) throughout the blood coagulation process. In vivo FXa can be generated either by activation via the extrinsic pathway, i.e. activation by factor VIIa, or via the intrinsic pathway, i.e. activation by activated coagulation factors IX (FIXa) and VIII (FVIIIa). The molecule undergoes enzymatic cleavage of the Arg15-Ile16 bond, liberating a 52-amino acid activation peptide. In presence of its cofactor, coagulation Factor Va (FVa), calcium (Ca) ions and negatively charged phospholipid membranes FXa assembles with those to a prothrombin (FII) activating complex (Toso et al. 2008).

Apart from these natural activation pathways there are several in-vitro procedures using trypsin (Bajaj et al. 1973) or non-human activators derived either from Russel's viper venom (Fujikawa et al. 1974), from fungal (Ruchel et al. 1983), bacterial (Imamura et al. 1997) or plant (Richter et al. 2002) sources. WO 2008/145989 A1 teaches two techniques for activation of FX to FXa by using venoms, in particular Russell's Viper Venom, as FX activator in combination with calcium ions. Russell's Viper Venom contains the substances RVV-V and RVV-X, which directly activate factor V and FX. RVV-X is a Zn2+ dependent serine protease. In the first technique, FX is incubated in a solution containing 25 mM calcium chloride and 0.01 U/ml of (RVV-X). In contrast in the second technique, RVV-X is immobilized on activated Sepharose® and contact FX. The resin was subsequently removed, while FXa remained in the supernatant. As a consequence, the addition of snake derived activator demands efficient means to remove potential leachables (venom) from the FXa preparation, in particular if the use in humans is intended. Additional separation techniques are necessary to minimize concerns about safety and tolerability of final product.

WO 2016/025601 A1 describes a FX activation process not relying on venom activators, but uses auto-activation of FX bound to an AEX resin (Q-Sepharose®), wherein bound FX is in contact with calcium ion containing solutions for several hours before being eluted from the resin. The yield of FXa eluted from the AEX resin was about 5% of co-eluted FX, which is not satisfactory for a production process.

Thus, an activation procedure using synthetically prepared activators with pharmaceutical grade quality resulting in high reproducible conversion would be a significant breakthrough in the field.

FXa is physiologically generated close to the end of the coagulation cascade, presenting a protease essential for conversion of prothrombin (FII) to thrombin (FIIa) and thus for conversion of fibrinogen to fibrin, which is responsible for wound closure and haemostasis: Located downstream of FVIII in the cascade, FXa as such can drive coagulation in principle also in the absence of FVIII or inhibited FVIII, thus can be regarded to reveal 'factor eight bypassing activity'.

Based on its factor eight bypassing activity FXa may be used for treatment of Hemophilia A patients. Haemophilia A is an x-chromosomally linked hereditary disease, which causes severe bleeding by the absence or dysfunctional coagulation factor VIII. During treatment of hemophilia patients, frequently the progressive development of neutralizing alloantibodies is reported (Kempton 2009). Such high titer inhibitor patients cannot be efficiently treated with coagulation factor VIII (FVIII) substitution, since applied FVIII is neutralized by those inhibitors. Patients suffer from episodes of bleeding and can be treated with an activated prothrombin complex concentrate (aPCC) (Kempton 2009). aPCC's comprise a complex mixture of coagulation factors, partly activated, and other plasma proteins. Another method of treatment is the application of activated coagulation factor VII (rFVIIa), which is produced recombinantly. rFVIIa enables direct activation of FX on the surface of platelets (Kempton 2009). By application of FVIII often in combination with immunomodulatory substances and/or a by-passing product, induction of immunotolerance (ITI) was achieved in 70% of patients receiving a regular and prolonged treatment, (Kempton 2009).

Since the amplification pathway is impaired in hemophilia A and B patients, blood coagulation is prolonged and blood loss is dramatically increased. Due to its central role in coagulation, FXa might temporarily restore normal clotting function. Furthermore, hemophiliacs suffering from neutralizing antibodies against their supplemented coagulation FVIII might be especially susceptible for treatment with FXa. Giles et al. (1988) found that a combination of phosphatidylcholine, phosphatidylserine and FXa has FVIII bypassing potential, but dosing seems to be critical for the net hemostatic outcome.

Another potential use of FXa is the reversal of Novel Oral Anticoagulants (NOACs) or Direct Oral Anticoagulants (DOACs), as these compounds are called more recently. One example of such a compound is rivaroxaban. Rivaroxaban, which is a direct reversible inhibitor of FXa is used for anticoagulant treatment of patients suffering from non-valvular atrial fibrillation and venous thromboembolism. Patients treated with DOACs like rivaroxaban have to undergo a systemic reversal of DOACs in case of a surgery (Lindhoff-Last 2017).

SUMMARY OF THE INVENTION

The inventors have surprisingly identified that plasma-derived FX can be converted to FXa/n-vitro in a composition with concentrations of the extrinsic and intrinsic activators, i.e. FVIIa, FIXa and FVIIIa, below the detection limit without the addition of proteinaceous activators, such as RVV-X. The risk of carry-over of such proteinaceous activators into the final product is thus eliminated. The activation is achieved by contacting a FX containing composition with synthetic phosphatidylserine (PS) and calcium.

According to a first aspect the present invention provides a process for activating FX to FXa, wherein the process is performed in-vitro and comprises the following steps:
a. providing a composition containing FX; and
b. contacting said FX with PS, in particular synthetic PS (sPS), and calcium to form an activation composition; and
c. incubating the activation composition to allow a conversion from FX to FXa.

This activation process according to the first aspect can in particular be a part of a process of production of a FXa composition. Thus, according to a second aspect the invention provides a process for production of a FXa composition comprising the process of activating FX to FXa according to the first aspect and further comprising at least one purification step.

Furthermore, the inventors have identified that after activation of FX to FXa remaining FX can be specifically removed from the composition without reducing the amount of FXa by using a heparin affinity column, in particular with a Heparin-Sepharose® resin. Thus, according to a third aspect the invention relates to a process for removing FX from a solution containing FX and FXa, comprising the following steps:
   a. contacting the solution containing FX and FXa with a heparin-affinity resin, in particular a Heparin-Sepharose® resin, under conditions suitable for binding of FXa, in particular at a pH in the range of 5.8 to 9.0;
   b. separating the heparin-affinity resin from the solution;
   c. optionally washing the heparin affinity resin; and
   d. optionally eluting the FXa from the heparin affinity resin under conditions suitable for elution.

According to a fourth aspect the invention relates to the use of the Heparin-Sepharose® resin for the removal of either FXa or FX from a composition containing FXa and FX.

Finally, according to a fifth aspect the invention relates to a FXa composition prepared according to the process of the second aspect.

DETAILED DESCRIPTION

Activation Process

Figure 1A:
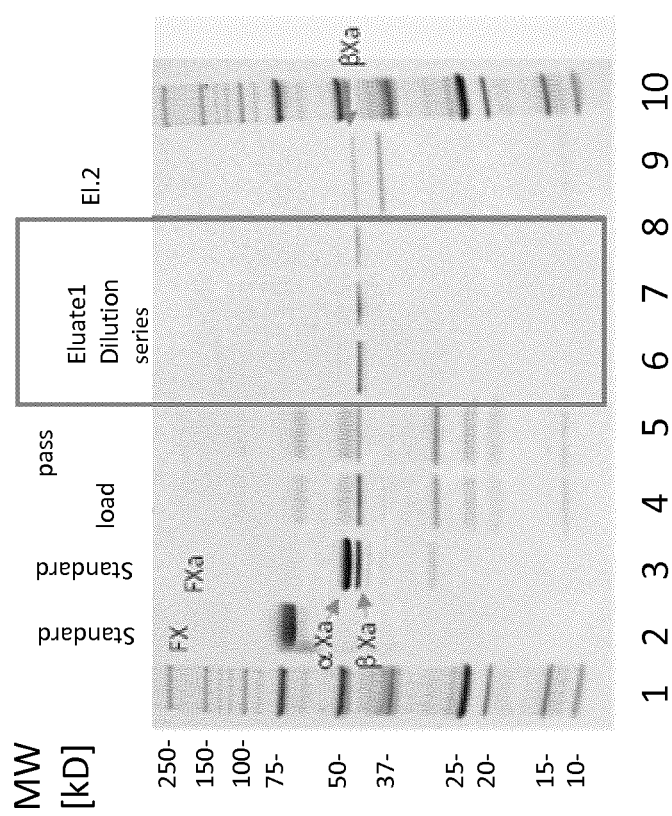
FIG. 1 depicts a SDS-Page (Coomassie blue stained) and a Western Blot (probed with a polyclonal antibody to FXa; Abcam #111171) under non-reducing conditions.
   Lane 1+10: Molecular weight marker
   Lane 2: commercial FX product (Coagadex®)
   Lane 3: commercial, plasma derived FXa standard (Coachrom) —a mixture of α-FXa and β-FXa.
   Lane 4: material loaded on Heparin Sepharose® HP column
   Lane 5: Flow through (pass) of Heparin Sepharose® HP column
   Lanes 6-8: Dilution series of Heparin Sepharose® HP Eluate 1 (0.25M NaCl)
   Lane 9: Heparin Sepharose® HP Eluate 2 (El.2; 1M NaCl)
   Immunoreactive bands for coagulation factor FXa were detected at approx. 50 kDa in lanes 4 to 9 (compare to α-FXa/β-FXa standard in lane 3). Especially lanes 6-8, depicting the Heparin Sepharose® eluate 1 showed a pure, single band β-FXa. Whereas the load and pass fractions (lanes 4 & 5) contained various other immunoreactive FX/FXa species. These signals were likely to represent FX proenzyme and activation fragments as well as truncated FX/FXa. Furthermore, the eluate 2 (lane 9) contained FXa in presence of a smaller, immune reactive species, most likely a truncated form of FXa.
Figure 1B:
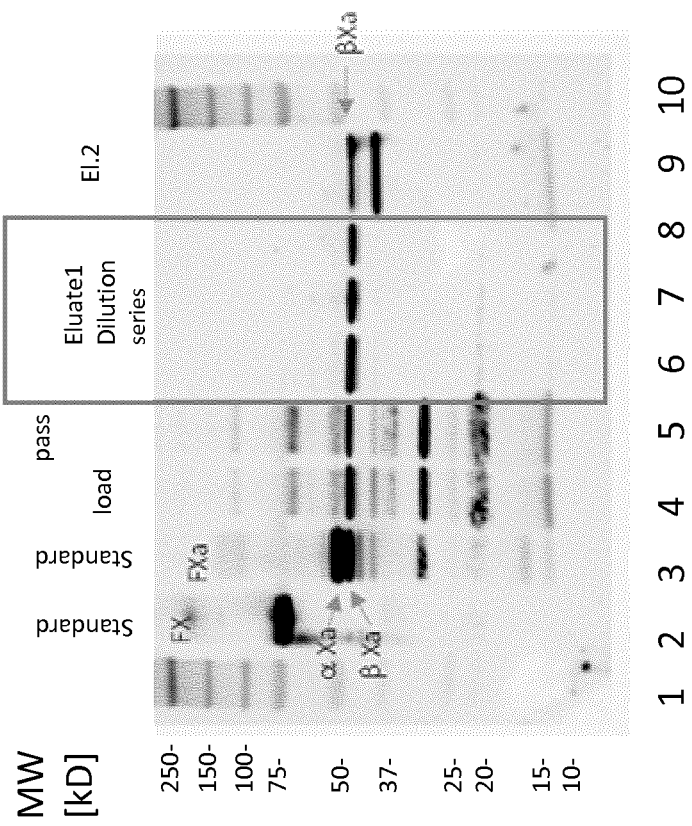
Figure 2:
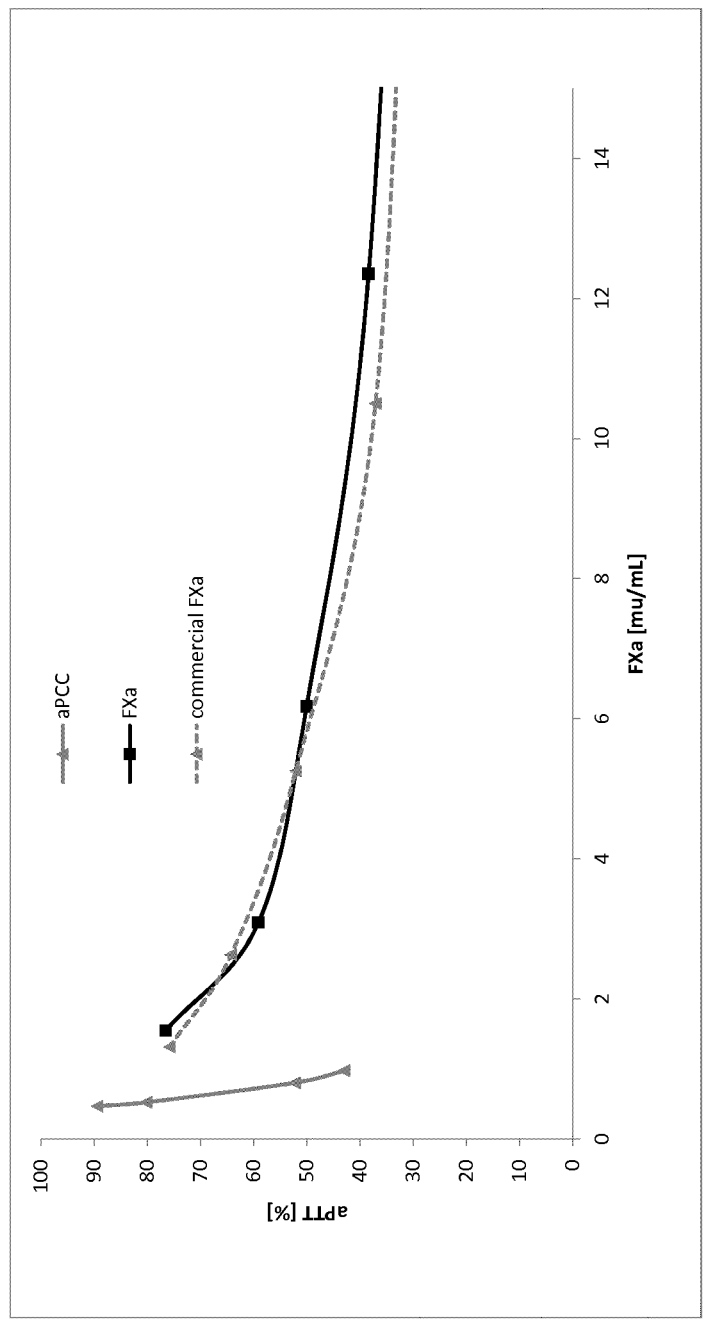
FIG. 2 depicts a comparison of FXa, purified by methods described in this patent, with a commercially available activated prothrombin complex concentrate (aPCC), which was manufactured from plasma derived FX, activated with Russel's Viper Venom (RVV) and purified. The graph shows aPTT reduction [%] in factor VIII inhibitor plasma as a function of FXa concentration. FXa, purified by methods described in this patent, showed very similar, dose dependent characteristics in the aPTT test system compared to commercially available FXa.
Figure 3:
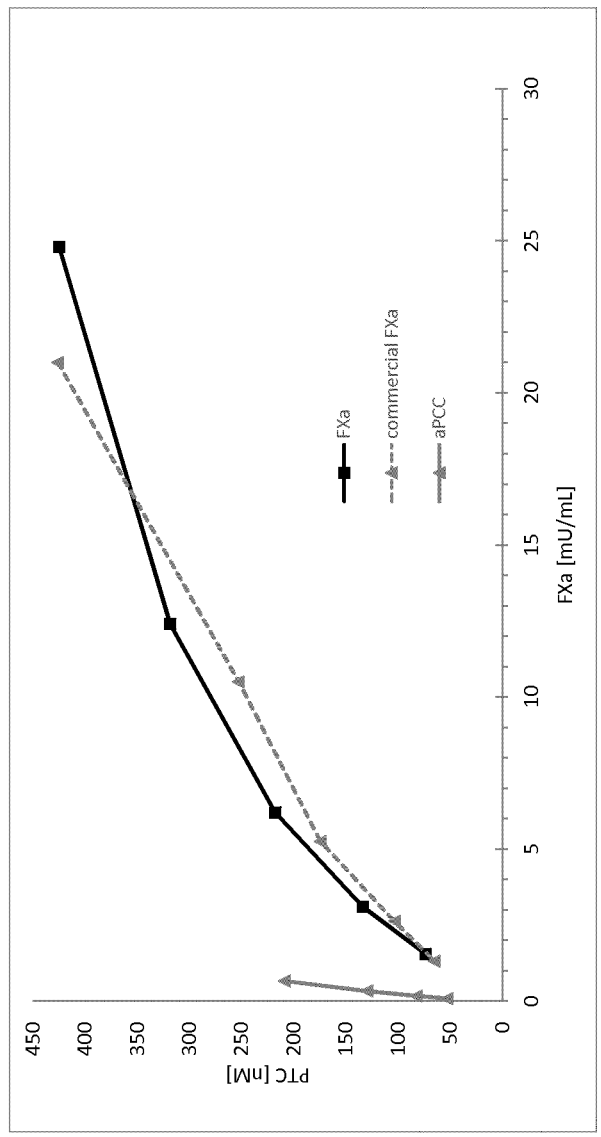
FIG. 3 depicts a comparison of FXa, purified by methods described in this patent, with a commercially available preparation, which was manufactured from plasma derived FX, activated with RVV and purified. The graph shows TGA mediation in factor VIII inhibitor plasma as a function of FXa concentration. FXa, purified by methods described in this patent, showed very similar, dose dependent characteristics in the TGA test system compared to commercially available FXa.
Figure 4:
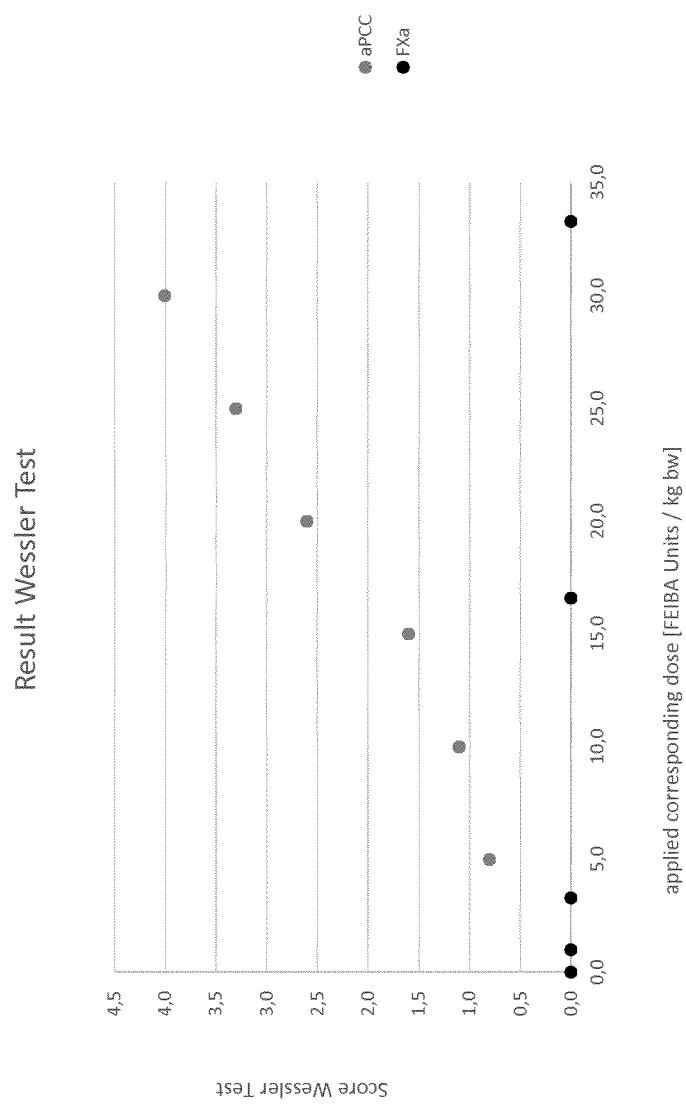
FIG. 4 depicts the results of FXa, prepared by methods described in this patent, in the safety test for thrombogenicity adverse effects in comparison with a commercially available and licensed activated prothrombin complex concentrate (aPCC) product. In contrast to a dose-dependent increase of the thrombogenic potential in an aPCC product, the pure FXa did not cause any thrombogenic issues.

The first aspect of the present invention is a process for activating FX to FXa, wherein the process is performed in vitro and comprises the following steps:
   a. providing a composition containing FX; and
   b. contacting said FX with (PS) and calcium to form an activation composition; and
   c. incubating the activation composition to allow a conversion from FX to FXa.

The process for activating FX to FXa is also referred as the "activation process". The process is in particular an in-vitro process. The composition containing FX is also referred to as the FX composition. "Contacting" as used herein means that the components are brought into the same composition to allow the components to contact each other. For contacting of the FX with the PS and calcium and formation of the activation composition, any known method of mixing components can be used. Moreover, the components FX, synthetic phosphatidylserine and calcium can be added in any possible sequence. For example, PS and calcium may be mixed in a composition and this composition may be added to the composition containing FX to form the activation composition. Alternatively, for both the PS and the calcium a solution can be prepared. In this regard, in one embodiment first the calcium and afterwards the PS is added to the composition containing FX. According to an alternative embodiment, first the PS and afterwards the calcium is added to the composition containing FX. According to a further alternative embodiment all components except the FX composition of the activation composition are premixed and the FX composition is added to this mixture.

The term "comprise", as used herein, besides its literal meaning, also includes the expressions "consist essentially of" and "consist of". Thus, the expression "comprise" refers to embodiments wherein the subject matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including the expressions "consist essentially of" and "consist of".

According to one embodiment, the composition containing FX is a manufacturing intermediate, in particular an intermediate of a process of manufacturing of a blood protein product. The FX composition is preferably an intermediate of a process of manufacturing of a FX or FXa product. The manufacturing of coagulation factors is based on a purification process, starting either from blood plasma or from a recombinant production source. Accordingly, the FX composition is preferably a purification intermediate. According to one embodiment, the FX is plasma derived. According to one embodiment, the FX composition is a blood plasma fractionation product. The composition containing FX may be derived from a side-fraction of blood plasma fractionation, which can be used as starting material for the activation process. Such side-fractions of blood plasma fractionation may be derived from processes as described by Hoffer et al. (1995) or Roemisch and Pock (2012). An already virus inactivated side-fraction is particularly beneficial for pathogen safety and solvent/detergent (S/D) treatment can be mentioned as one example of virus inactivation.

As stated above, the process does not require the addition of proteases or other proteins to the activation composition. Thus, according to one embodiment of the activation process, no proteinaceous activator is added. In particular, before and during the incubation of the activation composition no proteinaceous activator is added to the composition (s). More preferably also after the incubation no proteinaceous activator is added. As used herein, a "proteinaceous activator" is any peptide, in particular polypeptide that may activate FX. Proteinaceous activators are preferably FX specific serine proteases, such as FVIIa, FVIIIa and FIXa, or snake venom derived serine proteases, such as RVV-X.

Generally, the starting concentration of FX in the activation composition is not limited to a certain range. The concentration of FX changes over time during the activation process as it is converted into FXa. Thus, the concentration of FX at the time of mixture of the components is referred to as "starting concentration". For an effective conversion, the starting concertation of FX is preferably in the range from 2 to 80 IU/ml. The FX starting concentration in the activation composition may be 2 IU/ml, 3 IU/ml, 4 IU/ml, 5 IU/ml, 6 IU/ml, 7 IU/ml, 8 IU/ml, 9 IU/ml. 10 IU/ml at 12 IU/ml, 15 IU/ml, 20 IU/ml, 25 IU/ml, 30 IU/ml, IU/ml or 40 IU/ml, 45 IU/ml, 50 IU/ml, 55 IU/ml, or 60 IU/ml. Preferably, the starting concentration of FX in the activation composition is in the range of 2 to 40 IU/ml. More preferably, the starting concentration of FX in the activation composition is in the range of 5 to 25 IU/ml.

Phosphatidylserine (abbreviated Ptd-L-Ser or PS) is a phospholipid and is a component of the cell membrane. Synthetic PS (sPS) is a PS that is synthesized in-vitro using chemical synthesis or biotechnology. The PS used is preferably a synthetic PS. According to one embodiment the concentration of PS in the activation composition is in the range of 0.1 to 100 mg/ml. According to a further embodiment, the concentration of PS in the activation composition is in the range of 0.1 to 50 mg/ml. The PS concentration may be 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.8 mg/ml, 1 mg/ml, 2 mg/ml, 3 mg/ml, 4 mg/ml, 5 mg/ml, 7 mg/ml, 10 mg/ml, 12 mg/ml, 15 mg/ml, 17 mg/ml, 20 mg/ml, 25 mg/ml, 30 mg/ml, 35 mg/ml or 40 mg/ml or 45 mg/ml. Moreover, the concentration of PS in the activation composition may be in the range of 0.2 to 10 mg/ml. Preferably, the concentration of PS in the activation composition is in the range of 0.2 to 1 mg/ml.

According to one embodiment, the calcium used in the activation process is in the form of ions, in particular $Ca^{2+}$. According to one embodiment, preferably the calcium is added to the FX in the form of a salt selected from calcium phosphate, calcium chloride, or calcium citrate.

According to one embodiment, the concentration of the calcium ions in the activation composition is in the range of 1 to 100 mM. The concentration may be 1 mM, 2 mM, 3 mM, 4 mM, 5 mM, 7 mM, 10 mM, 12 mM, 15 mM, 17 mM, 20 mM, 25 mM, 30 mM, 35 mM, 40 mM 45 mM, 50 mM, 55 mM, 60 mM, 65 mM, 70 mM, 75 mM or 80 mM. According to one embodiment the concentration of the calcium ions in the activation composition is in the range of 2.5 to 50 mM. According to one embodiment, the concentration of the calcium ions in the activation composition is in the range of 5 to 40 mM. According to a preferred embodiment, the concentration of the calcium ions in the activation composition is in the range of 10 to 35 mM.

According to one embodiment of the process for activating FX to FXa, the pH of the activation composition is in the range of 5.0 to 9.0. The pH may be 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. According to one embodiment, the pH in the activation composition is in the range of 6.0 to 8.0. Preferably, the pH is in the range of 7.3 to 7.7.

According to one embodiment of the process for activating FX to FXa, the temperature of the activation composition during incubation is in the range of 15 to 40° C. The Temperature may be 15° C., 16° C., 17° C., 18° C., 19° C., 20° C., 15° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. Preferably, the incubation temperature is in the range from 15 to 35° C. More preferably, the incubation temperature is about room temperature.

During the activation process, FX is converted to FXa. Thus, the components of the activation composition changes over time until an equilibrium is reached or the process is stopped. With regard to FX and FXa the terms "conversion" and "activation" are used interchangeably. According to one embodiment, the activation process is stopped after a defined time, i.e. the "incubation time" or "activation time". According to one embodiment, the activation process may be, in particular, stopped by the addition of EDTA.

According to a further embodiment of the first aspect, the incubation time is in the range of 1 to 48 hours. The incubation time may be 1 h, 2 h, 3, 4 h, 5 h, 6 h, 7 h, 8 h, 9 h, 10 h, 11 h, 12 h, 13 h, 15 h, 16 h, 17 h, 18 h, 19, 20 h, 21 h, 22 h, 23 h, 24 h, 25 h, 26 h, 27 h, 28 h, 29 h, 30 h, 32 h, 34 h, 36 h, 38 h, 40 h, 42 h, 44 h, or 46 h. Preferably, the incubation time is in the range of 4 to 20 hours.

As shown in the examples with a process according to the first aspect, the yield of conversion from FX to FXa is at least 10%. As used herein, yield of conversion from FX to FXa or "FX conversion yield" identifies the percentage of FX molecules converted to FXa, i.e. the number of FXa molecules at the end of the activation process to the number of FXa molecules at the start of the activation process. Depending on the conditions, conversion yields of up to 100% may be achieved with the activation process. The yield of conversion may be at least 20%, at least 30%, at least 40%, at least 50%, at least 60%, at least 70%, at least 80%, or at least 90%. According to one embodiment of the first aspect, they FX Conversion yield is in the range of 20% to 100%.

According to one embodiment, the composition containing FX further contains FII. As shown in the examples, when FII is present in the activation composition it is converted to FIIa. This shows that the identified conditions according to the first aspect are suitable for a conversion of the FII (prothrombin) to FIIa (thrombin) by FXa. According to one embodiment, the starting concentration of FII in the activation composition is in the range of 0.01 to 80 IU/ml. The FII starting concentration in the activation composition may be 0.01 IU/ml, 0.05 IU/ml, 0.1 IU/ml, 0.5 IU/ml, 1 IU/ml, 2 IU/ml, 3 IU/ml, 4 IU/ml, 5 IU/ml, 7 IU/ml, 8 IU/ml, 10 IU/ml, 12 IU/ml, 15 IU/ml, 17 IU/mi, 20 IU/mi, 25 IU/mi, 30 IU/mi, 35 IU/mi, 40 IU/mi, 45 IU/mi, 50 IU/mi, 55 IU/mi, 60 IU/ml, 65 IU/ml, 70 IU/ml, or 75 IU/ml. Preferably, the starting concentration of FII in the activation composition is in the range of 0.01 to 40 IU/ml. More preferably, the starting concentration of FII in the activation composition is in the range of 2 to 25 IU/ml. According to a further embodiment the starting concentration of FII is in the range of 0.01 to 2 IU/ml. According to a further embodiment the starting concentration of FII is in the range of 0.1 to 0.8 IU/ml.

According to one embodiment of the first aspect, the concentration of the intrinsic and extrinsic activators of FX in the composition containing FX are below detection limit. In particular, the concentration of FVII/FVIIa, FVIII/FVIIIa and FIX/FIXa in the composition containing FX is below the detection limit as determined by chromogenic assays.

The composition containing FX may be an initial protein mixture containing 1-80 IU/ml FX, in particular 1-60 IU/ml, and 0.03-80 IU/ml FII, in particular 0.03-60 IU/ml, with a total protein content of more than 0 up to 60 mg/ml in a biologically acceptable buffer in the pH range of 6-8. The total protein can also be in a range of 1 to 50 mg/ml. The total protein may further be in a range of 2 to 25 mg/ml. Such an initial protein mixture can be obtained from affinity-chromatography, for example heparin-affinity chromatography. Persons skilled in the art know biologically acceptable buffers well, as examples might be mentioned buffers based on citrate, phosphate, TRIS or imidazole. One example of an acceptable buffer is a buffer containing 20 mM TRIS and 150 mM NaCl at a pH of 7.5±0.2. Initial protein mixtures with above indicated content of total protein, FX and FII can be used as starting material in the activation process.

According to a further embodiment of the first aspect of the present invention, the initial protein mixture is derived from blood plasma fractionation or biotechnological FX manufacturing, obtained by recombinant or transgenic expression and immuno-affinity chromatography.

The blood plasma fraction for generation of the initial protein mixture is preferably cryo-poor plasma.

Initial protein mixtures may contain about 40 IU/ml FX and 0.01-80 IU/ml FII with a total protein content of 1-60 mg/ml in a buffer consisting of 20 mM TRIS and 150 mM NaCl at pH=7.5.

The initial protein mixtures may be obtained by subjecting the blood fraction a DEAE-Sepharose or heparin affinity chromatography and a buffer exchange.

The cryo poor plasma may be stabilized by heparin and is adsorbed to the anion exchange resin QAE-Sephadex. After washing, Vitamin K dependent factors are eluted with a buffer of elevated ionic strength. For example, the ion strength may be 1600-2200 mosmol/kg. The Vitamin K dependent factors in the eluate are stabilized by addition of 3 IU heparin/ml. The stabilized eluate may further be subjected to S/D treatment by 0.3% TnBP/1% Polysorbate 80 incubation. If so, the S/D reagents may be removed by adsorption on DEAE-Sepharose and washed with a buffer of 260-310 mosmol/kg. The proteins may then be eluted in a buffer of 700-780 mosmol/kg. The elutate may then be subjected to a buffer exchange by ultra-/diafiltration e.g with a 10 kDa membrane. The new buffer may have about 330-400 mosmol/kg. The buffer exchange may be followed by a concentration to 30 IU Factor IX/ml.

Alternatively, the cryo-poor plasma may be adsorbed on an anion exchange resin, such as DEAE-Sephadex A50, and the resin is afterwards washed. An eluate may be obtained by elution with a buffer of high ionic strength of 2 M sodium chloride and 15 mM sodium citrate at about neutral pH. The eluate may be concentrated to 380-420 mosmol/kg. The (concentrated) eluate may be subjected to anion exchange purification on a DEAE resin, such as DEAE-Sepharose FF. After washing, the DEAE-eluate may be obtained with a buffer of 360 mM sodium chloride, 5 mM sodium citrate and 5 mM disodium hydrogen phosphate. The DEAE-eluate may be subjected to virus inactivation by 0.3% TnBP/1% Polysorbate 80 incubation. Thereafter, the S/D treated eluate may be subjected to affinity chromatography on Heparin-Sepharose CL 6B. After washing with a buffer consisting of 20 mM sodium citrate with a pH of 7.0-8.0 an eluate may be obtained by elution with a buffer consisting of 250 mM sodium chloride, 20 mM sodium citrate having the same pH.

For obtaining the initial protein mixture, each of purification processes may be followed by a buffer exchange using ultra-/diafiltration with membrane having a cut-off of 10 kDa to a buffer consisting of 20 mM TRIS and 150 mM NaCl at pH=7.5.

When starting with a recombinant expression product, in particular immune recombinant affinity chromatography may be used to obtain the initial protein mixture. Specifically an antibody specific for FX and/or FXa, e.g.: Origene®/Acris® Calcium dependent monoclonal antibody to coagulation factor X and Xa; Cat. No.: AX100083, may be immobilized to an activated chromatography resin like NHS-Sepharose®. A column containing this immuno-affinity resin can be preconditioned with an equilibration buffer containing 5-100 mM TRIS, 1-250 mM NaCl, 10-25 mM Ca-ions and 0.005-1% of a non-ionic surfactant, like Polysorbate, at a pH value of 7.0-8.0 and a conductivity of 1-50 mS/cm, an acceptable equilibration buffer may contain 10-40 mM TRIS, 100-150 mM NaCl, 5-20 mM Ca-ions and 0.01-0.2% Polysorbate at a pH value of 7.4±0.2 and a conductivity of about 10 to 25 mS/cm. Buffer exchange to the equilibration buffer can be performed with the initial protein mixture prior to loading onto the immuno-affinity column. After thoroughly washing with equilibration buffer the flow-through/wash fraction containing unbound impurities is discarded and bound FX is eluted from the column with an elution buffer containing 5-100 mM TRIS, 1-250 mM NaCl, 1-200 mM EDTA and 0.005-1% non-ionic surfactant at a pH of 6.0-8.0, preferred elution buffers contain 10-40 mM TRIS, 100-150 mM NaCl, 20-60 mM EDTA and 0.01-0.2% Polysorbate at a pH of 7.4±0.2. Thus obtained initial protein mixture is brought to a FX content of 5-80 IU/ml, in particular to 30-50 IU/ml, by ultra-/diafiltration with a buffer consisting of 5-100 mM TRIS, 50-500 mM NaCl and 0.005-1% non-ionic surfactant at pH of 6.0-8.0, acceptable buffers may contain 10-40 mM TRIS, 130-170 mM NaCl and 0.01-0.2% Polysorbate at pH of 7.5±0.2, and a membrane having a cut-off of 10 kDa. It is possible to activate this initial protein mixture with one of the activation methods selected from examples 1 to 4 and 9 without necessity for further purification afterwards. Thus, obtained initial protein mixture can also be used as starting material in the activation process.

The risk of carry-over of these compounds into the final product is thus eliminated. The initial protein mixtures can be activated at various conditions in the presence of a phosphatidylserine dispersion (PS dispersion), in particular a dispersion of synthetic phosphatidylserine. PS dispersion can be prepared with a concentration of 0.1-100 mg/mL of synthetic phosphatidylserine in a biologically acceptable buffer containing 5-100 mM buffer compound, e.g. maleate, imidazole, carbonate or TRIS, and 5-500 mM NaCl at a pH range of 6.0-8.0. Buffers containing 10-40 mM TRIS and 130-170 mM NaCl at a pH of 7.5±0.2 are in particular well suited and are used as reaction buffer. PS can be dispersed in the buffer by high shear mixing, for instance with an Ultraturrax® dispenser, for about 1-240 minutes at 20-60° C., to achieve the majority of dispersed particles with a diameter of less than <25 µm, in particular of less than <10 µm, followed by cooling down to room temperature. Other techniques well known for those skilled in the art of phospholipid vesicles preparation are for instance lipid film hydration, detergent removal, reverse phase evaporation and organic solvent infusion and can be used for preparation as well. The final dispersion can be subjected to subsequent steps to further reduce particle size like sonication or extrusion.

In one embodiment of the first aspect, an initial protein mixture can be mixed with PS dispersion and a solution of Ca-ions to obtain a mixture containing 1-25 mg/ml total protein, 1-30 IU/ml FX, 0.003-0.3 U/ml FII, 0.1-2 mg/ml PS and 2.5-50 mM Ca-ions and the pH may be adjusted to a range of 5.0-9.0, in particular to a pH of 7.4 to 7.6. The mixture can be incubated at 15-40° C., for 1-48 hours, in particular for 4-16, even more particular for 4-10 hours at 15-35° C., with gentle stirring, followed by addition of a buffer additionally containing a chelating agent, like EDTA, or any other chelating agent capable of effectively hindering Ca-ions of further activation of FX to FXa. 50 mM of EDTA will for example be sufficient to hinder effectively 25 mM Ca-ions of further activation of FX to FXa. After incubation and EDTA addition dispersed PS is dissolved by adding 0.01-10% of a surfactant, e.g. Triton X-100, sodium deoxycholate or CHAPS, in order to obtain a clear or almost clear solution, which can be filtered via a 0.2-1.0 µm filter, in particular a 0.45 µm filter, to recover a FXa containing intermediate. FXa analytics were performed at this stage of the process.

Thus prepared mixtures have a FXa-specific activity, as defined in the assay description, of 1-30 IU/ml and thrombin levels <50 IU/ml, with FXa yield of about 25-100%, in particular 30-75%, based on the FX content subjected to activation with PS and Ca-ions.

In one embodiment of the first aspect an initial protein mixture, containing 1-50 mg/ml total protein, 1-60 IU/ml FX and 0.03-60 U/ml FII, is diluted with reaction buffer. The amount of the reaction buffer is about 90% of the amount of the initial protein mixture, and additionally admixed is a reaction buffer containing about 75 mM Ca-ions. The amount of the reaction buffer containing Ca-ions is the same as the amount of the undiluted initial protein mixture. A PS dispersion, the amount being about 10% of the undiluted initial protein mixture, is added cautiously under continuous steering to above described mixture and the pH may be adjusted to a range of 5.0-9.0, in particular to a pH of 7.4 to 7.6. The obtained mixture containing PS can be incubated at 15-40° C., in particular at 15-35° C., for 1-48 hours, in particular 4-20 hours, with gentle stirring, followed by addition of reaction buffer additionally containing a chelating agent. Stopping the activation of FX to FXa, dissolving PS dispersion and filtration in order to recover a FXa containing intermediate can be performed as described in the first embodiment.

Thus prepared mixture have a FXa-specific activity of 1-60 IU/ml, less than 10000 IU/ml FIIa and about 9.9 mg/ml total protein content, with FXa yield of about 30-75% based on the FX content subjected to activation with PS and Ca-ions.

Production Process

According to a second aspect, the invention provides a process for production of a FXa composition comprising the process of activating FX to FXa according to the first aspect and further comprising at least one purification step.

According to one embodiment of the second aspect, the at least one purification step is selected from the group of immobilized metal affinity chromatography (IMAC), anion exchange chromatography (AEX) and affinity chromatography (AF). The AF may be in particular an immune-affinity chromatography or a heparin-affinity chromatography.

The production process according to the second aspect may include a variety of purification steps. Suitable methods for the protein purification steps are, for example, IMAC, AEX, cation exchange chromatography (CEX), AF, in particular an immune-affinity chromatography or a heparin-affinity chromatography, size exclusion chromatography (SEC). The methods can be used in any combination and sequence. Between the purification steps, for the steps for example for buffer exchange May be included, such as diafiltration or ultra/diafiltration (UDF). The activation process may be performed before the purification steps, in between two purification steps or after the purification steps, i.e. on the purification product.

According to one embodiment, the process of production starts with the activation process according to the first aspect and is followed by an AEX. In one embodiment of the second aspect, a column packed with an anion exchange resin, the resin may be selected from weak or strong anion exchange resins, as one example Q-Sepharose® may be mentioned was preconditioned with a biologically acceptable equilibration buffer in the pH range of 5.8-8.0. Persons skilled in the art know such biologically acceptable buffers well, as examples might be mentioned buffers based on citrate, TRIS or imidazole. Equilibration buffers may contain 1-100 mM imidazole at a pH range of 6.1-7.0 and a conductivity of 1-20 mS/cm. The FXa containing intermediate can be diluted or buffer exchanged with the equilibration buffer until the conductivity is below 20 mS/cm. This diluted FXa solution can be loaded onto the preconditioned anion exchange column in order to bind FXa while unbound proteins and impurities, like thrombin and PS, are in the flow through and the following wash fraction. The column can thoroughly be washed with a buffer by decreasing pH in the range of 5.8-8.0 or increasing conductivity or a combination of both. Such a washing buffer may contain 1-100 mM imidazole and 0.1-0.3 M NaCl at a pH of 5.8-7.0 until the monitored OD280 readings of the UV flow cell is back at base line level. FXa can be eluted from the anion exchange resin with a biologically acceptable elution buffer in the pH range of 5.8-9.0. Either by decrease of pH and/or increase of conductivity, bound proteins can be eluted. An elution buffer containing 1-100 mM TRIS and at least 0.3 M NaCl, in particular 0.3-1.5 M NaCl, at a pH of 5.8-9.0 can be used therefore.

Subsequently, the anion exchange eluate can be diluted to a diluted eluate containing 1-30 mM, preferably 1-3 mM, imidazole and 0.4-4 M NaCl, preferably 0.5-1 M, NaCl at a pH range of 5.8-9.0, preferably 7.4±0.2.

The AEX may then be succeeded by an IMAC. In one embodiment of the second aspect, the diluted eluate from the anion exchange column is loaded onto an Immobilized Metal Affinity Chromatography (IMAC) resin charged with copper ions. FXa is found under these conditions in the IMAC flow through fraction and can be obtained therefrom with a purity of 20-45 U/mg protein, while impurities like alpha-2-macroglobulin, inter-alpha-trypsin inhibitor, Protein C or vitronectin bind to the resin.

Optionally the IMAC may be followed by a heparin-affinity chromatography, in particular using a Heparin-Sepharose® resin. In one embodiment of the second aspect, the buffer of the IMAC flow through fraction is exchanged in order to obtain FXa solubilized in a 1-100 mM TRIS buffer at a pH of 5.8-9.0, in particular 6.8-8.0. The obtained FXa solution can be subjected to heparin-affinity chromatography over a Heparin-Sepharose® resin, which had been equilibrated with a buffer containing 1-100 mM TRIS and 0.0005-1% of a non-ionic surfactant, such as Polysorbate, at a pH range of 5.8-9.0, in particular 6.8-8.0. FXa binds under these conditions to the resin while zymogen FX and impurities such as F1.2, which is an activation fragment of FII, pass the column unbound. After washing with equilibration buffer and return of the monitored OD280 signal to base line FXa can be eluted from the resin by increasing the conductivity. Such an elution buffer can contain 1-100 mM TRIS 0.0005-1% of a non-ionic surfactant, such as Polysorbate, and 0.01-0.30 M NaCl at a pH range of 5.8-9.0, in particular 6.8-8.0. FXa eluted from the Heparin-Sepharose® resin has a purity of 80-217 U/ml, in particular 150-210 U/ml.

In an alternative embodiment of the second aspect the AEX is succeeded by an immune-affinity chromatography with a FX/FXa-specific immuno-affinity resin. In this regard, a column containing a FX/FXa-specific immuno-affinity resin, described prior, is preconditioned with an equilibration buffer containing 5-100 mM TRIS, 1-250 mM NaCl, 10-25 mM Ca-ions and 0.005-1% of a non-ionic surfactant at a pH value of 7.0-8.0 and a conductivity of 1-250 mS/cm. An acceptable equilibration buffer may contain 10-40 mM TRIS, 100-150 mM NaCl, 5-20 mM Ca-ions and 0.01-0.2% Polysorbate at a pH value of 7.4±0.2 and a conductivity of about 10 to 20 mS/cm. Buffer exchange to the equilibration buffer is performed with the eluate of the anion exchange chromatography prior to loading onto the immuno-affinity column. After thoroughly washing with equilibration buffer the flow-through/wash fraction containing unbound impurities is discarded and bound FXa is eluted from the column with an elution buffer containing 5-100 mM TRIS, 1-250 mM NaCl, 5-40 mM EDTA and 0.005-1% Polysorbate at a pH of 7.4±0.2 and a conductivity of 1-250 mS/cm. In particular, such an elution buffer may contain 10-40 mM TRIS, 100-150 mM NaCl, 10-40 mM EDTA and 0.05% Polysorbate at a pH of 7.4±0.2 and a conductivity of 19±2 mS/cm. FXa eluted from the FX/FXa-specific immuno-affinity resin had a purity of more than 95%.

Optionally, the immune-affinity chromatography may be followed by a heparin-affinity chromatography, in particular using a Heparin-Sepharose® resin. In one embodiment of the second aspect, FXa is eluted from the immuno-affinity resin and further purified with Heparin-Sepharose® above wherein FX is separated from FXa, if desired.

In one embodiment of the second aspect of the present invention, a column containing a FX/FXa-specific immuno-affinity resin, described prior, is preconditioned with an equilibration buffer containing 5-100 mM TRIS, 1-250 mM NaCl, 10-25 mM Ca-ions and 0.005-1% of a non-ionic surfactant at a pH value of 7.0-8.0 and a conductivity of 1-250 mS/cm. An acceptable equilibration buffer may contain 10-40 mM TRIS, 100-150 mM NaCl, 5-20 mM Ca-ions and 0.01-0.2% Polysorbate at a pH value of 7.4±0.2 and a conductivity of about 10 to 25 mS/cm. Buffer exchange to the equilibration buffer is performed with the initial protein mixture prior to loading onto the immuno-affinity column. After thoroughly washing with equilibration buffer the flow-through/wash fraction containing unbound impurities is discarded and bound FX is eluted from the column with an elution buffer containing 5-100 mM TRIS, 1-250 mM NaCl, 5-40 mM EDTA and 0.005-1% Polysorbate at a pH of 7.4±0.2 and a conductivity of 1-50 mS/cm. In particular, such an elution buffer may contain 10-40 mM TRIS, 100-150 mM NaCl, 10-40 mM EDTA and 0.05% Polysorbate at a pH of 7.4±0.2 and a conductivity of 19±2 mS/cm. After buffer exchange FX eluted from the immuno-affinity column can be activated by one of the activation processes described prior obtaining a mixture of FX and FXa with their ratio being dependent on activation yield.

In one embodiment of the second aspect, FX is eluted from the immuno-affinity resin and activated with the process according to the first aspect and further purified with Heparin-Sepharose®.

Process of Removal of FX

According to a third aspect, the invention relates to a process for removing FX from a solution containing FX and FXa, comprising the following steps:
a. contacting the solution containing FX and FXa with a heparin-affinity resin, in particular a Heparin-Sepharose® resin, under conditions suitable for binding of FXa, in particular at a pH in the range of 5.8 to 9.0;
b. separating the heparin-affinity resin from the solution;
c. optionally washing the heparin affinity resin; and
d. optionally eluting the FXa from the heparin affinity resin under conditions suitable for elution.

This process can be used in combination with the activation process of the first aspect. However, the process may be used for any composition comprising both FXa and FX. The process may also be used to remove FXa from a solution containing FX and FXa. Thus, according to an alternative embodiment of the third aspect the invention relates to a process for removing FX from a solution containing FX and FXa, comprising the following steps:
a. contacting the solution containing FX and FXa with a heparin-affinity resin, in particular a Heparin-Sepharose® resin, under conditions suitable for binding of FXa, in particular at a pH in the range of 5.8 to 9.0;
b. separating the heparin-affinity resin from the solution;
c. collecting the FX containing solution;
d. optionally washing residual amounts of FX off the heparin affinity resin; and
e. optionally using the FX containing solutions obtained in step c) and optionally d) for further working up.

As used herein "removal" or "removing" means the reduction of the concentration of the component to be removed in a composition. Removal is not limited to but specifically includes the possibility of a complete elimination of the component from the composition.

The pH of the contacting step is in the range of 5.8 to 9.0. The pH may be 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. Preferably, the pH is in the range of 6.8 to 8.0.

The composition in which the heparin is contacted with the FX/FXa preferably further comprises 0.0005-1% of a non-ionic surfactant. The percentage of non-ionic surfactant may be, for example, 0.0005%, 0.001%, 0.005%, 0.01%, 0.05%, 0.1%, 0.5% or 1%. Preferably, the non-ionic surfactant may be for example Polysorbate.

The composition preferably comprises 1-100 mM TRIS. TRIS may be present, for example, in a concentration of 1 mM, 2 mM, 3 mM, 4 mM, 5 mM, 7 mM, 10 mM, 12 mM, 15 mM, 17 mM, 20 mM, 25 mM, 30 mM, 35 mM, 40 mM, 45 mM, 50 mM, 55 mM, 60 mM, 65 mM, 70 mM, 75 mM, 80 mM. Preferably the non-ionic surfactant may be for example Polysorbate.

FXa binds under these conditions to the resin while zymogen FX and impurities such as F1.2, which is an activation fragment of FII, pass the column unbound.

For elution of the FXa from the column a higher salt concentration can be used. According to one embodiment the elution buffer contains salt in a concentration of 0.01 to 0.30 M. The salt is preferably NaCl. The elution buffer may contain NaCl in a concentration of, for example, 0.01 M, 0.02 M, 0.03 M, 0.05 M, 0.07 M, 0.1 M, 0.12 M, 0.15 M, 0.17 M, 0.2 M, 0.22 M, 0.25 M, 0.27 M or 0.3 M.

For example, the composition containing FXa and FX is solubilized in a 1-100 mM TRIS buffer at a pH of 5.8-9.0, in particular 6.8 to 8.0. The obtained FXa solution can be subjected to heparin-affinity chromatography over a Heparin-Sepharose® resin, which had been equilibrated with a buffer containing 1-100 mM TRIS and 0.0005-1% of a non-ionic surfactant, such as Polysorbate, at a pH range of 5.8-9.0, in particular 6.8-8.0. FXa binds under these conditions to the resin while zymogen FX and impurities such as F1.2, which is an activation fragment of FII, pass the column unbound. After washing with equilibration, buffer and return of the monitored OD280 signal to base line FXa can be eluted from the resin by increasing the conductivity. Such an elution buffer can contain 1-100 mM TRIS 0.0005-1% of a non-ionic surfactant, such as Polysorbate, and 0.01-0.30 M NaCl at a pH range of 5.8-9.0, in particular 6.8-8.0. FXa eluted from the Heparin-Sepharose® resin has a purity of 80-217 U/ml, in particular 150-210 U/ml.

The process according to the third aspect can also be used to remove FXa from a FX composition. According to a fourth aspect the invention relates to the use of the Heparin-Sepharose® resin for the removal of either FXa or FX from a composition containing FXa and FX. For the use according to the fourth aspect the same conditions defined for the third aspect apply.

According to one embodiment of the second aspect, the production process contains a heparin affinity chromatography defined according to third aspect and an activation process according to the first aspect.

Composition and Use in Medical Treatment

According to a fifth aspect, the present invention provides a FXa composition prepared according to the process of the second aspect.

According to one embodiment, in the FXa composition of the fifth aspect, the ratio of FXa to FX is more than 10:1. Preferably, the ratio of FXa to FX is more than 20:1. More preferably, the ratio of FXa to FX is more than 50:1. According to one embodiment of the fifth aspect, the composition further comprises FIIa. Preferably, the ratio of FIIa to FXa is in the range from 1:30 to 1:5000.

Pathogen safety of the FXa containing preparation is accomplished by incorporation of pathogen removal or inactivation steps, such as solvent/detergent treatment, nanofiltration or other means known by the skilled person, or a combination thereof at appropriate places in the production process. The FXa intermediates obtained by one of the processes described in the third aspect of the present invention were formulated by ultra-/diafiltration (UDF) with a formulation buffer based on 5-100 mM of biologically and pharmaceutically acceptable buffer substance e.g. histidine, citrate, citrate-phosphate, phosphate, succinate or other, 10-300 mM NaCl or other salt, eventually with 0.001-0.5%$_{w/v}$ non-ionic surfactant, such as polysorbate or poloxamer or polymer like albumin, Prionex® or polyethylene glycol serving as a stabilizer.

Such a formulation is eventually complemented by one or more excipients and stabilizers selected from saccharides, sugar alcohols, polyols, amino acids, polymers or other biocompatible compounds, like sucrose, trehalose, glucose, lactose, maltitol, mannitol, glycine, L-arginine or PVP (polyvinyl pyrrolidon, for example Kollidon® 12 PF or 17 PF). According to one embodiment, the FXa composition of the fifth aspect further comprises stabilizers selected from saccharides, polyols, amino acids, polymers or polyvinyl pyrrolidon (PVP).

The pH range of the FXa composition is preferably in the range of 6.0-7.5. The formulated FXa composition is stored frozen or can be brought to a final FXa concentration of 0.05-10 IU/ml prior to lyophilization. Examples of such formulations are presented in Table 1.

In particular, the FXa composition of the fifth aspect may be formulated and eventually lyophilized to be used immobilized in or on a carrier material useful in the local treatment of bleeding disorders or for local initiation of blood coagulation. Thus, according to one embodiment of the fifth aspect, FXa composition is a lyophilized composition. According to one embodiment, the FXa composition is stable for at least 48 hours after reconstitution. Alternatively, the FXa composition is stored frozen.

According one embodiment of the fifth aspect, the FXa composition is for use in the treatment of a bleeding disorder. The bleeding disorder can be hemophilia A, hemophilia B, von Willebrand disease, congenital hemophilia A with inhibitors or acquired hemophilia A with inhibitory auto antibodies to FVIII, congenital hemophilia B with inhibitors or acquired hemophilia B with inhibitory auto antibodies to FIX, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease with inhibitors to von Willebrand factor, or combinations thereof.

According one embodiment of the fifth aspect, the bleeding disorder is caused by administration of novel oral anticoagulants (NOACs) or direct oral anticoagulants (DOACs).

The present invention enables production of FXa for the management of NOAC-/DOAC-induced bleeding events during surgery or injury of patients receiving oral anticoagulation in an economical and pathogen save process. Due to the role of FXa in blood coagulation treatment of inherited and acquired bleeding deficiencies it is also possible with a preparation comprising a mixture of FXa and FIIa, which is also obtainable by a process of the present invention, to manage bleedings induced by NOACs/DOACs belonging to the group of direct thrombin inhibitors.

Usage of biologically acceptable buffers, like buffers based on citrate, phosphate, TRIS, imidazole and many more, is in general preferred.

In order to confirm the stability and activity of the reconstituted FXa preparations of the present invention, lyophilized compositions were reconstituted to their initial volume and subjected to analytical testing, in particular to determination of FXa-specific activity and thrombin generation (TGA) in FVIII-Inhibitor Plasma. FXa-specific activity testing revealed preservation of more than 75% and TGA testing of more than 85% of the initial activity after lyophilization. The results are presented in Table 2.

Selected formulations 1, 2 and 6 were reconstituted and stored as a liquid for 48 hours at room temperature, in particular 20-25° C., and at 2-8° C. for determination of residual activity after liquid storage. After 48 hours of liquid storage at room temperature FXa-specific activity testing revealed preservation of more than 90% and TGA testing of more than 85% of the activity of the reconstituted preparations prior to liquid storage. Results are summarized in Table 3.

According to one embodiment, the use comprises administering the FXa composition via a parenteral application method, such as intravenous injection or infusion. The compositions obtained by the inventive process may be applied intravenously, but local and topical application is also possible.

In patients treated with direct oral anticoagulants, immobilized and locally applied FXa, i.e. not intravenously applied FXa, or a mixture containing FXa and FIIa may enable restoration of normal coagulation function limited to the site of treatment. Since FXa and FIIa are target molecules for direct oral anticoagulants, immobilized FIIa and/or FXa locally applied would scavenge the excess of inhibitors and restore local action of intrinsic FXa and FIIa. Furthermore, immobilized FIIa would initiate coagulation of blood at the site of injury and form a primary clot. The FXa containing composition can be immobilized on or in a coated or soaked sponge, patch, film, bandage or other carrier material commonly used, like a powder or a granulate for local administration.

According to one embodiment of the fifth aspect, the use comprises administering the composition locally via a coated or soaked sponge, patch, film, bandage or other carrier material commonly used, like a powder or a granulate. For local application hemostatic means, like films, patches, bandages or sponges, soaked with a composition of the present invention or on which the composition is deposited on the surface of said means are suitable for stopping local bleedings. Said hemostatic means are also suitable for locally stopping bleedings of patients under anticoagulant treatment with DOACs, in particular, if thrombin was additionally deposited on or in the means.

The compositions obtained by the inventive process have low thrombotic potential as evidenced by aPTT determination, thrombin generation assay (TGA) and an animal study related to determine the outcome of a Wessler test (Wessler et al. 1959) and are presented in Table 4.
Analytics (FX/FXa and FII/FIIa)

The obtained product and intermediates were subjected to analytical testing, namely FX ELISA, TGA (thrombin generation assay), FXa-specific activity assay and a FIIa-specific chromogenic assay. Although chromogenic substrates for the determination of FXa and FIIa are very specific for each protease, but not 100%, a minor portion of cleavage of potential other targets occurs, especially at high protease concentrations. In order to determine the FXa-/FIIa-specific activity, highly specific inhibitors for FXa (i.e.: Rivaroxaban) and FIIa (i.e.: dabigatran) were used to determine the inhibitable amount, representing the protease-specific activity, of the respective protease. Activation efficacy was calculated and expressed as percentage of FXa generated from total FX added into reaction.
TGA—Thrombin Generation Assay Prediluted samples (Dilution buffer: 20 mM TRIS, 130 mM NaCl, 0.5% human serum albumin (HSA); pH 7.4) were mixed with FVIII inhibitor plasma (Technoclone; Mat. No. 5159008) in a ratio of 1 part prediluted sample+4 parts inhibitor plasma and immediately subjected to measurement. The measurement was performed according to manufacturer's instructions using the Technothrombin TGA kit (Technoclone; Technothrombin RC high kit; Mat. No.: 5006010). The read-out parameter was peak thrombin concentration (PTC) in nM.
FXa-Specific Activity Assay (Measurement of FXa in Presence of Cross-Reactive Proteins)

The FXa-specific activity assay was used for measurement of FXa in presence of cross-reactive proteins. FXa containing samples and standards were diluted with dilution buffer (50 mM TRIS, 0.2% BSA (bovine serum albumin); pH 8.4). Conversion of chromogenic substrate CS11(32) (Biophen®) in diluted samples was measured for 5 minutes on a temperature controlled micro plate reader (405 nm) with and without addition of 10 mM rivaroxaban. The assay was calibrated with a FXa concentrate (Coachrom purified human factor Xa; EZ007A). The FXa-specific activity contained in each sample was calculated by subtraction of non-inhibitable activity, measured in samples treated with rivaroxaban, from total activity, measured in samples without rivaroxaban. Thrombin, if being present at high concentrations, e.g. 1000 U/ml, cleaves also substrates specific to FXa and mimics false high FXa activity.
FIIa-Specific Activity Assay (Measurement of FIIa in Presence of Cross-Reactive Proteins)

The FIIa-specific activity assay was used for measurement of FIIa in the presence of considerable concentrations of proteins, which may also cleave the thrombin chromogenic substrate, although at a relatively low rate. Thrombin containing samples and standards were diluted with dilution buffer (50 mM TRIS, 100 mM NaCl, 1% PEG 6000; pH 8.3). Conversion of chromogenic substrate CS01(38) (Biophen®) in diluted samples was measured for 5 minutes on a temperature controlled micro plate reader (405 nm) with and without addition of 10 µM dabigatran (incubation at 37° C. for 30 minutes). The assay was calibrated with a bovine thrombin reagent as in house standard against WHO standard generation 2 (01/580). The thrombin-specific activity contained in each sample was calculated by subtraction of non-inhibitable activity, measured in samples treated with dabigatran, from total activity, measured in in samples without dabigatran. The assay can also be performed with hirudin as inhibitor.
Total Protein Total protein was determined with a Bradford assay from Pierce® according to manufacturer's instructions.
Measurement of FII and FX FII and FX measurements in not activated mixtures were performed with assays from Instrumentation Laboratories (IL) according to manufacturer's instructions on an ACL instrument.
Measurement of FX:Ag FX measurements in activated mixtures were performed with a Hyphen Zymutest® FX (#RKO33A) assay according to manufacturer's instructions.
SDS PAGE:

SDS PAGE, using 4-20% acrylamide gradient gels, was performed under non-reducing conditions according to manufacturer's instructions for the Novex® gel system (Thermo Scientific; Novex®).
Western Blotting:

SDS PAGE (4-20% acrylamide gradient gels) and electro transfer were performed under non reducing conditions according to manufacturer's instructions for Novex® gel system and XCell II Item and XCThermo Scientific). The membrane was blocked with Super Block (TBS)® ready to use blocking buffer manufactured by Thermo Scientific. Thereafter, the membrane was probed with a polyclonal anti FX/FXa antibody (polyclonal antibody to FXa; Abcam #111171) diluted in blocking buffer. As secondary antibody, a suitable antibody with HRP label was used, also diluted in blocking buffer. Probed proteins were detected using Super Signal Pico® (Thermo Scientific) ECL substrate and a time series of images was recorded.

EXAMPLES

Starting Material from Blood Plasma Purification

Initial protein mixtures containing about 40 IU/ml FX and 0.01-80 IU/ml FII with a total protein content of 1-60 mg/ml in a buffer consisting of 20 mM TRIS and 150 mM NaCl at pH=7.5.

The initial protein mixtures were obtained from a DEAE sepharose or heparin affinity chromatography side-fraction from coagulation factor purification and a buffer exchange by ultra-/diafiltration.

Specifically, heparin stabilized cryo-poor plasma was allowed to adsorb to the anion exchange resin QAE-Sephadex and the resin was washed afterwards. Vitamin K dependent factors were then eluted with a buffer having elevated ionic strength of 1600-2200 mosmol/kg and stabilized by addition of 3 IU heparin/ml. The stabilized eluate was subjected to S/D treatment by 0.3% TnBP/1% Polysorbate 80 incubation, and the S/D reagents were removed by adsorption on DEAE-Sepharose and washing with a buffer of 260-310 mosmol/kg. The proteins were eluted with a buffer of 700-780 mosmol/kg. Finally, the initial protein mixture was obtained by buffer exchange with a buffer of about 330-400 mosmol/kg over a 10 kDa membrane using Ultra-/Diafiltration and concentration to 30 IU Factor IX/ml.

Alternatively, cryo-poor plasma was allowed to adsorb to DEAE-Sephadex A50, and the resin was washed afterwards. An eluate obtained by elution with a buffer of high ionic strength of 2 M sodium chloride and 15 mM sodium citrate at about neutral pH was concentrated to 380-420 mosmol/kg and the concentrated eluate was subjected to anion exchange purification using DEAE-Sepharose FF. After washing, the DEAE-eluate was obtained with a buffer of 360 mM sodium chloride, 5 mM sodium citrate and 5 mM disodium hydrogen phosphate and the DEAE-eluate subjected to virus inactivation by 0.3% TnBP/1% Polysorbate 80 incubation. Thereafter, the S/D treated eluate was subjected to affinity chromatography on Heparin-Sepharose CL 6B. After washing with a buffer consisting of 20 mM sodium citrate with a pH of 7.0-8.0 an eluate was obtained by elution with a buffer consisting of 250 mM sodium chloride, 20 mM sodium citrate having the same pH.

For obtaining the initial protein mixture, each of purification processes was followed by a buffer exchange using ultra-/diafiltration with membrane having a cut-off of 10 kDa to a buffer consisting of 20 mM TRIS and 150 mM NaCl at pH=7.5.

Starting Material from Blood Plasma Purification or Biotechnological FX Manufacturing Obtained with Immune-Affinity Chromatography An antibody specific for FX and FXa was immobilized to an activated chromatography resin like NHS-Sepharose®. A column containing this immuno-affinity resin was preconditioned with an equilibration buffer containing 20 mM TRIS, 130 mM NaCl, 10 mM Ca-ions and 0.05% Polysorbate 80 at a pH value of 7.4 and a conductivity of 16.8 mS/cm. Buffer exchange to the equilibration buffer was performed with the initial protein mixture prior to loading onto the immuno-affinity column. After thoroughly washing with equilibration buffer the flow-through/wash fraction containing unbound impurities was discarded and bound FX was eluted from the column with an elution buffer containing 20 mM TRIS, 130 mM NaCl, 40 mM EDTA and 0.05% Polysorbate 80 at a pH of 7.4 and a conductivity of 19.2 mS/cm. Thus obtained initial protein mixture was brought to a FX content of about 40 IU/ml by ultra-/diafiltration with a buffer consisting of 20 mM TRIS and 150 mM NaCl at pH=7.5 and a membrane having a cut-off of 10 kDa. It was possible to activate this initial protein mixture with one of the activation methods selected from examples 1 to 4 and 9 without necessity of further purification.

Example 1 (Activation)

40 mg of synthetic phosphatidylserine (SPS) were mixed with 10 ml of reaction buffer (20 mM TRIS and 150 mM NaCl at pH=7.5), dispersed with an Ultraturrax® dispenser for 30 minutes at 50° C. and cooled to room temperature to obtain an SPS dispersion.

55 ml of the initial protein mixture, containing 2 mg/ml total protein, about 40 IU/ml FX and about 0.5 U/ml FII, was mixed with 27.5 ml of SPS dispersion, 27.5 ml of reaction buffer and 55 ml of reaction buffer containing 75 mM Ca-ions. The mixture with a pH of 7.5 was incubated at room temperature for 6 hours with gentle stirring, followed by addition of 55 ml of reaction buffer with 200 mM EDTA. Dispersed PS was dissolved by adding 1.5 mM Triton X-100 and the obtained clear solution was filtered via a 0.45 µm PES membrane filter to recover a FXa containing intermediate.

Thus prepared mixtures had a FXa-specific activity, as defined in the assay description, of about 9.6 IU/ml and thrombin levels of <50 IU/ml, with a FXa yield of about 69% based on the FX content subjected to activation with PS and Ca-ions.

Example 2 (Activation)

100 ml of initial protein mixture, containing 40 mg/ml total protein, about 60 IU/ml FX and about 60 U/ml FII, was mixed with 90 ml of reaction buffer and 100 ml of reaction buffer containing 75 mM Ca-ions. 10 ml of PS dispersion were added dropwise under continuous steering. The mixture with a pH of 7.0 was incubated at 22° C. for 16 hours with gentle stirring, followed by addition of 100 ml of reaction buffer with 200 mM EDTA. Dispersed PS was dissolved by adding 1.5 mM Triton X-100 and the obtained clear solution was filtered via a 0.45 µm PES membrane filter to recover a FXa containing intermediate.

Thus prepared mixture had a FXa-specific activity of 8.2 IU/ml, a FIIa-specific activity of 619 IU/ml and 9.9 mg/ml total protein content. With FXa yield of 33% based on the FX content subjected to activation with PS and Ca-ions.

Example 3 (Activation)

Initial protein mixture was diluted with reaction buffer, mixed with PS dispersion and Ca-ions to obtain a solution containing 40 IU/ml FX, 0.33 mg/ml PS and 25 mM Ca-ions. This mixture was incubated at 15° C. with gentle steering for 10 hours before the reaction was stopped with 50 mM EDTA. Dispersed PS was dissolved by adding 1.5 mM Triton X-100 and the obtained clear solution was filtered via a 0.45 μm PES membrane filter to recover a FXa containing intermediate.

Thus prepared mixture had a FXa-specific activity of 4.1 IU/ml, a FIIa-specific activity of 3.1 IU/ml and 0.4 mg/ml total protein content and a FXa yield of 41% based on the FX content subjected to activation with PS and Ca-ions.

Example 4 (Activation)

Part of the reaction mixture of example 3 prior to incubation was withdrawn and used for a 10 hours incubation at 33° C. The outcome of this activation process resulted in 2.8 IU/mL FXa, 16.4 IU/mL FIIa, 0.6 mg/mL protein content and FX/FXa conversion yield 27% based on the FX content subjected to activation with PS and Ca-ions.

Example 5 (Capture of FXa and Removal of FIIa—AEX)

A column packed with the strong ion exchange resin Q-Sepharose® was preconditioned with an equilibration buffer containing 10 mM Imidazole at a pH of 6.3 and a conductivity of 1.0 mS/cm. The FXa containing intermediate was diluted with the equilibration buffer until the conductivity was below 15.0 mS/cm. This diluted FXa solution was loaded onto the preconditioned anion exchange column in order to bind FXa while unbound proteins and impurities, like thrombin and PS, were in the flow through and the following wash fraction. The column was thoroughly washed with a washing buffer containing 10 mM Imidazole and 0.2 M NaCl at a pH of 6.3 and a conductivity of 21.4 mS/cm until the monitored OD280 readings of the UV flow cell were back at base line level. FXa was eluted from the anion exchange resin with an elution buffer containing 20 mM TRIS and 1 M NaCl at a pH of 7.4 and a conductivity of 89.3 mS/cm. The obtained anion exchange eluate had a purity of 8 U of FXa per mg protein.

Example 6 (Removal of Copper-Binding Proteins—IMAC)

The anion exchange eluate was diluted with a buffer containing 20 mM TRIS and 4 mM Imidazole at a pH of 7.4 in order to decrease NaCl content from 1 M to 0.5 M and adjust imidazole concentration to 2 mM. This diluted eluate was loaded onto an Immobilized Metal Affinity Chromatography (IMAC) resin charged with copper ions and FXa being present in the IMAC flow through fraction had a purity of 43 U/mg protein.

Example 7 (Separation of FXa from FX by Heparin-Affinity Chromatography)

The buffer of the IMAC flow through fraction was exchanged in order to obtain FXa solubilized in a 20 mM TRIS buffer at a pH of 7.4 and a conductivity of 1.6 mS/cm and the obtained FXa solution was subjected to Heparin-affinity chromatography over a Heparin-Sepharose® HP resin, which had been equilibrated with a buffer containing 20 mM TRIS and 0.005% Polysorbate 80 at a pH of 7.4 and a conductivity of 1.6 mS/cm. FXa bound under these condition to the resin while zymogen FX and impurity F1.2 passed the column unbound. After washing with equilibration buffer and return of monitored OD280 signal to base line FXa was eluted from the resin with an elution buffer containing 20 mM TRIS, 0.005% Polysorbate 80 and 0.25 M NaCl at a pH of 7.4 and a conductivity of 26.1 mS/ml. FXa eluted from the Heparin-Sepharose® HP resin had a purity of 199 U/ml.

Example 8 (Immuno-Affinity Chromatography—Activation)

A column containing a FX/FXa-specific immuno-affinity resin with Origene®/Acris® Calcium dependent monoclonal antibody to coagulation factor X and Xa (Cat. No.: AX100083) covalently bound was preconditioned with an equilibration buffer containing 20 mM TRIS, 130 mM NaCl, 10 mM Ca-ions and 0.05% Polysorbate 80 at a pH value of 7.4 and a conductivity of 16.8 mS/cm. Buffer exchange to the equilibration buffer was performed with the initial protein mixture, which was not obtained from immune-affinity chromatography, prior to loading onto the immuno-affinity column. After thoroughly washing with equilibration buffer the flow-through/wash fraction containing unbound impurities was discarded and bound FX and FXa was eluted from the column with an elution buffer containing 20 mM TRIS, 130 mM NaCl, 40 mM EDTA and 0.05% Polysorbate 80 at a pH of 7.4 and a conductivity of 19.2 mS/cm.

Example 9 (Formulation)

The FXa intermediates were formulated by ultra-/diafiltration (UDF) with a basic formulation buffer containing 10 mM histidine, 100 mM NaCl and 0.005% w/v Polysorbate, complemented by one excipient, as can be seen in Table 1, at a pH of 7.2. The formulated FXa compositions were brought to a final FXa concentration of 0.3 IU/ml and a protein content of less than 0.125 mg/ml prior to lyophilization.

Example 10 (Lyophilization)

Several preparations of purified FXa were formulated for lyophilization with the buffers given in Table 1 and filled in vials. The FXa formulations in the vials were subjected to a lyophilization cycle ensuring a residual water content of less than 1.5% determined by the method of Karl Fischer (Karl Fischer 1935).

Results

TABLE 1

| Formulation | Formulation Buffer |
| --- | --- |
| 1 | 10 mM histidine, 100 mM NaCl, pH 7.2, 0.005% w/v Polysorbate |
| 2 | 10 mM histidine, 100 mM NaCl, pH 7.2, 0.005% w/v Polysorbate, 2.5% sucrose |
| 3 | 10 mM histidine, 100 mM NaCl, pH 7.2, 0.005% w/v Polysorbate, 2.5% trehalose |
| 4 | 10 mM histidine, 100 mM NaCl, pH 7.2, 0.005% w/v Polysorbate, 2.5% PVP (Kollidon 12 PF) |
| 5 | 10 mM histidine, 100 mM NaCl, pH 7.2, 0.005% w/v Polysorbate, 2.5% maltitol |
| 6 | 10 mM histidine, 100 mM NaCl, pH 7.2, 0.005% w/v Polysorbate, 2.5% mannitol |
| 7 | 10 mM histidine, 100 mM NaCl, pH 7.2, 0.005% w/v Polysorbate, 100 mM L-arginine |

TABLE 2

| Tested Parameter | Sample | Formulation 1 | 2 | 3 | 4 | 5 | 6 | 7 |
|---|---|---|---|---|---|---|---|---|
| FXa-specific activity (IU/ml) | Before Lyo | 0.32 | 0.33 | 0.34 | 0.33 | 0.34 | 0.35 | 0.34 |
| | After Lyo | 0.29 | 0.30 | 0.27 | 0.30 | 0.30 | 0.37 | 0.32 |
| | Residual % | 90.6 | 90.9 | 79.4 | 90.9 | 88.2 | 105.7 | 94.1 |
| PTC (nM) diluted 1:10 in TGA assay | Before Lyo | 121.6 | 136.2 | 124.6 | 125.0 | 131.7 | 140.2 | 119.9 |
| | After Lyo | 119.7 | 119.6 | 114.7 | 121.8 | 123.5 | 146.0 | 149.7 |
| | Residual % | 98.4 | 87.8 | 92.1 | 97.4 | 93.8 | 104.1 | 124.9 |

TABLE 3

| | FXa-specific activity (IU/ml) | | | | | PTC (nM) diluted 1:10 in TGA assay | | | | |
|---|---|---|---|---|---|---|---|---|---|---|
| Formulation | Start | After 24 h. (2-8° C.) | After 48 h. (2-8° C.) | After 24 h. (RT) | After 48 h. (RT) | Start | After 24 h. (2-8° C.) | After 48 h. (2-8° C.) | After 24 h. (RT) | After 48 h. (RT) |
| 1 | 0.3 | 0.33 | 0.33 | 0.33 | 0.33 | 167.4 | 174.3 | 169.2 | 158.9 | 157.5 |
| 2 | 0.34 | 0.34 | 0.34 | 0.35 | 0.34 | n.d. | n.d. | n.d. | n.d. | n.d. |
| 6 | 0.40 | 0.40 | 0.41 | 0.40 | 0.40 | 215.9 | 200.5 | 196.5 | 197.7 | 194.7 |

TABLE 4

Results of Wessler safety test for thrombogenicity

| Test item | FEIBA U/kg bw | mean score |
|---|---|---|
| FXa | 33.3 | 0.0 |
| FXa | 16.6 | 0.0 |
| FXa | 3.3 | 0.0 |
| FXa | 1.0 | 0.0 |
| aPCC | 30.0 | 4.0 |
| aPCC | 25.0 | 3.3 |
| aPCC | 20.0 | 2.6 |
| aPCC | 15.0 | 1.6 |
| aPCC | 10.0 | 1.1 |
| aPCC | 5.0 | 0.8 |
| neg control | 0.0 | 0.0 |

REFERENCES

Toso et al. The conformational switch from the factor X zymogen to protease state mediates exosite expression and prothrombinase assembly; The Journal of Biological Chemistry, 2008; 283 (27): 18627-18635. —DOI: 10.1074/jbc.M802205200.

Bajaj, S. P. Mann, K. G. Simultaneous Purification of Bovine Prothrombin and Factor X.; J. Biol. Chem., 1973; 248(22): 7729-7741.

Fujikawa, K., Coan, M. H., Legaz, M. E. & Davie, E. W. The mechanism of activation of bovine factor X (Stuart factor) by intrinsic and extrinsic pathways; Biochemistry, 1974; 13: 5290-5299.

Rüchel, R. On the renin-like activity of Candida proteinases and activation of blood coagulation in vitro; Zentralblatt für Bakteriologie, Mikrobiologie und Hygiene 1. Abt. Originale A., 1983; 255: 368-379.

Imamura, T., Potempa, J., Tanase, S. & Travis, J. Activation of blood coagulation factor X by arginine-specific cysteine proteinase (Gingiparin-Rs) from Porphyromonas gingivalis.; Journal of Biological Chemistry, 1997; 272: 16062-16067.

Richter, G. et al. Activation and inactivation of human factor X by proteases derived from Ficus carica.; British Journal of Haematology, 2002; 19: 1042-1051.

Kempton and White. How we treat a hemophilia A patient with a factor VIII inhibitor; Blood, 2009; 113 (1): 11-17. —DOI: 10.1182/blood-2008-06-160432.

Giles, A. R. et al. A combination of factor Xa and phosphatidylcholine-phosphatidylserine vesicles bypasses factor VIII in vivo; British Journal of Haematology, 1988; 69: 491-497.

Lindhoff-Last, Edelgard. Direct oral anticoagulants (DOAC)—Management of emergency situations; Hamostaseologie, 2017; 37(04): 257-266. —DOI: 10.5482/HAMO-16-11-0043.

Hoffer, L., Schwinn, H., Biesert, L., Josic, D. Improved virus safety and purity of a chromatographically produced factor IX concentrate by nanofiltration.; Journal of chromatography. B, Biomedical applications, 1995; 669 (2): 187-196.

Roemisch J. and Pock, K. In: Production of Plasma Proteins for Therapeutic Use, J. Bertolini, N. Goss, and J. Curling (eds.), John Wiley & Sons Inc., Hoboken, New Jersey; 2012; 65-79.

Wessler et al. Biologic assay of a thrombosis-inducing activity in human serum; J. Appl. Physiol., 1959; 14(6): 943-946.

K. Fischer. Neues Verfahren zur maßanalytischen Bestimmung des Wassergehaltes von Flüssigkeiten und festen Körpern; Angewandte Chemie, 1935; 48: 394-396. —DOI:10.1002/ange.19350482605.

The invention claimed is:
1. A process for activating Coagulation Factor X (FX) to activated Coagulation Factor X (FXa), wherein the process is performed in vitro and comprises the following steps:
  a. providing a composition containing FX and FII; and b. contacting said composition with phosphatidylserine (PS) and calcium to form an activation composition; and
c. incubating the activation composition to allow a conversion from FX to FXa, wherein the yield of conversion from FX to FXa is in the range of 20%-100%, and wherein before, during and after incubation no proteinaceous activator is added to the composition(s).

2. The process for activating FX to FXa according to claim 1, wherein the FX is a plasma derived FX.

3. The process for activating FX to FXa according to claim 1, wherein the starting concentration of FX in the activation composition is in the range from 2 to 80 IU/ml.

4. The process for activating FX to FXa according to claim 1, wherein the concentration of phosphatidylserine in the activation composition is in the range of 0.05 to 100 mM.

5. The process for activating FX to FXa according to claim 1, wherein the calcium is in the form of ions, and the concentration of the calcium ions in the activation composition is in the range of 1 to 100 mM.

6. The process for activating FX to FXa according to claim 1, wherein the concentration of FII in the activation composition is in the range of 0.01 to 30 IU/ml.

7. The process for activating FX to FXa according to claim 1, wherein the pH of the activation composition is in the range of 5.0 to 9.0.

8. The process for activating FX to FXa according to claim 1, wherein the temperature of the activation composition during incubation is in the range of 15-40° C.

9. The process for activating FX to FXa according to claim 1, wherein the incubation time is in the range of 1 to 48 hours.

10. The process for activating FX to FXa according to claim 1, wherein the starting concentration of FX in the activation composition is in the range of 2 to 40 IU/ml.

11. The process for activating FX to FXa according to claim 1, wherein the concentration of phosphatidylserine in the activation composition is in the range of 0.1 to 50 mM.

12. The process for activating FX to FXa according to claim 1, wherein the concentration of phosphatidylserine in the activation composition is in the range of 0.2 to 10 mM.

13. The process for activating FX to FXa according to claim 1, wherein the concentration of phosphatidylserine in the activation composition is in the range of 0.2 to 1 mM.

14. The process for activating FX to FXa according to claim 1, wherein the calcium is in the form of ions, and the concentration of the calcium ions in the activation composition is in the range of 2.5 to 50 mM.

15. The process for activating FX to FXa according to claim 1, wherein the calcium is in the form of ions, and the concentration of the calcium ions in the activation composition is in the range of 5 to 40 mM.

16. The process for activating FX to FXa according to claim 1, wherein the calcium is in the form of ions, and the concentration of the calcium ions in the activation composition is in the range of 10 to 35 mM.

17. The process for activating FX to FXa according to claim 1, wherein the concentration of FII in the activation composition is in the range of 0.01 to 1 IU/ml.

18. The process for activating FX to FXa according to claim 1, wherein the pH of the activation composition is in the range of 7.4 to 7.6.

19. The process for activating FX to FXa according to claim 1, wherein the temperature of the activation composition during incubation is in the range of 15 to 35° C.

20. The process for activating FX to FXa according to claim 1, wherein the incubation time is in the range of 4 to 20 hours.

* * * * *